US008262570B2

(12) United States Patent
White et al.

(10) Patent No.: US 8,262,570 B2
(45) Date of Patent: Sep. 11, 2012

(54) RETRACTION APPARATUS AND METHOD OF USE

(75) Inventors: John White, Marquette, MI (US);
Phillip J. Berman, Negaunee, MI (US);
Matthew P. Gephart, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 330 days.

(21) Appl. No.: 12/475,067

(22) Filed: May 29, 2009

(65) Prior Publication Data
US 2009/0299148 A1 Dec. 3, 2009

Related U.S. Application Data

(60) Provisional application No. 61/057,639, filed on May 30, 2008.

(51) Int. Cl.
*A61B 1/32* (2006.01)
(52) U.S. Cl. .......................... 600/219; 600/224; 600/225
(58) Field of Classification Search .................. 600/210, 600/213, 215, 216, 218, 227, 231–233
See application file for complete search history.

(56) References Cited

U.S. PATENT DOCUMENTS

| | | | | |
|---|---|---|---|---|
| 2,383,705 A | * | 8/1945 | Bortagaray | 600/232 |
| 2,473,266 A | | 6/1949 | Wexler | |
| 2,623,517 A | | 12/1952 | Barlow et al. | |
| 2,893,378 A | * | 7/1959 | Cooper | 600/233 |
| 3,038,468 A | * | 6/1962 | Raeuchle | 600/233 |
| 3,168,093 A | * | 2/1965 | Gauthier | 600/232 |
| 3,509,873 A | * | 5/1970 | Karlin et al. | 600/226 |
| 3,724,449 A | * | 4/1973 | Gauthier | 600/215 |
| 3,948,259 A | | 4/1976 | Bolduc et al. | |
| 3,965,890 A | * | 6/1976 | Gauthier | 600/215 |
| 3,998,217 A | | 12/1976 | Trumbull et al. | |

(Continued)

FOREIGN PATENT DOCUMENTS

WO 03086202 10/2003

(Continued)

OTHER PUBLICATIONS

United States Patent and Trademark Office, Non-Final Office Action mailed Oct. 15, 2009 in U.S. Appl. No. 11/539,224 (17 pages).

(Continued)

*Primary Examiner* — Eduardo C Robert
*Assistant Examiner* — Jacqueline Johanas
(74) *Attorney, Agent, or Firm* — Fitch, Even, Tabin & Flannery, LLP

(57) ABSTRACT

A retraction apparatus and method are provided including slider assemblies for being slidably connected to a retractor body with end portions of the slider assemblies disposed within a central retractor opening. A retractor blade is slidably connected to one of the slider assembly end portions such that the depth of the retractor blade can be readily adjusted. Once the retractor blade is at the desired depth within the incision, a handle is pivoted to a locked position to fix the blade relative to the slider assembly. A cantilever lock between the blade and the slider assembly pivots the blade relative to the slider assembly to fix the blade thereto. In one form, the retractor body has a substantially flat surface configured to be placed adjacent a bone and slide connections which position slider assemblies such that the connected blades avoid contact with the bone during retraction.

21 Claims, 14 Drawing Sheets

U.S. PATENT DOCUMENTS

| | | | |
|---|---|---|---|
| 4,010,741 A * | 3/1977 | Gauthier | 600/234 |
| 4,434,791 A * | 3/1984 | Darnell | 600/233 |
| 5,520,610 A | 5/1996 | Giglio et al. | |
| 5,667,481 A | 9/1997 | Villalta et al. | |
| 5,688,223 A | 11/1997 | Rosendahl | |
| 5,728,046 A | 3/1998 | Mayer et al. | |
| 5,813,978 A | 9/1998 | Jako | |
| 5,928,139 A | 7/1999 | Koros | |
| 5,944,658 A | 8/1999 | Koros et al. | |
| 5,954,635 A | 9/1999 | Foley et al. | |
| 5,957,927 A | 9/1999 | Magee et al. | |
| 5,967,973 A * | 10/1999 | Sherts et al. | 600/233 |
| 6,083,154 A | 7/2000 | Liu et al. | |
| 6,139,493 A * | 10/2000 | Koros et al. | 600/215 |
| 6,206,826 B1 | 3/2001 | Mathews et al. | |
| 6,213,940 B1 | 4/2001 | Sherts et al. | |
| 6,224,545 B1 | 5/2001 | Cocchia et al. | |
| 6,322,500 B1 | 11/2001 | Sikora et al. | |
| 6,416,467 B1 | 7/2002 | McMillin et al. | |
| 6,464,634 B1 | 10/2002 | Fraser | |
| 6,468,207 B1 | 10/2002 | Fowler et al. | |
| 6,616,605 B2 | 9/2003 | Wright et al. | |
| 6,800,084 B2 | 10/2004 | Davison et al. | |
| 6,849,064 B2 | 2/2005 | Hamada | |
| 6,869,398 B2 | 3/2005 | Obenchain et al. | |
| 6,896,654 B2 | 5/2005 | Paolitto et al. | |
| 6,932,764 B2 | 8/2005 | Kashyap | |
| 7,195,592 B2 | 3/2007 | Ravikumar et al. | |
| 7,780,594 B2 * | 8/2010 | Hutton | 600/219 |
| 2002/0111538 A1 * | 8/2002 | Wright et al. | 600/233 |
| 2002/0193666 A1 * | 12/2002 | Sherts et al. | 600/231 |
| 2003/0191371 A1 | 10/2003 | Smith et al. | |
| 2004/0002629 A1 | 1/2004 | Branch et al. | |
| 2004/0087833 A1 | 5/2004 | Bauer | |
| 2004/0133077 A1 | 7/2004 | Obenchain et al. | |
| 2004/0133201 A1 | 7/2004 | Shluzas et al. | |
| 2004/0176665 A1 | 9/2004 | Branch | |
| 2004/0193018 A1 | 9/2004 | Thalgott et al. | |
| 2004/0230100 A1 | 11/2004 | Shluzas | |
| 2004/0242969 A1 | 12/2004 | Sherts et al. | |
| 2005/0080320 A1 | 4/2005 | Lee et al. | |
| 2005/0137461 A1 | 6/2005 | Marchek et al. | |
| 2005/0149035 A1 | 7/2005 | Pimenta et al. | |
| 2005/0159650 A1 | 7/2005 | Raymond et al. | |
| 2005/0159651 A1 | 7/2005 | Raymond et al. | |
| 2005/0192485 A1 | 9/2005 | Branch et al. | |
| 2005/0215862 A1 | 9/2005 | Larson et al. | |
| 2005/0215866 A1 | 9/2005 | Kim | |
| 2005/0234304 A1 | 10/2005 | Dewey et al. | |
| 2005/0261694 A1 | 11/2005 | Orton et al. | |
| 2005/0277812 A1 | 12/2005 | Myles | |
| 2006/0004261 A1 | 1/2006 | Douglas | |
| 2006/0030858 A1 | 2/2006 | Simonson et al. | |
| 2006/0052672 A1 | 3/2006 | Landry et al. | |
| 2006/0074445 A1 | 4/2006 | Gerber et al. | |
| 2007/0118022 A1 * | 5/2007 | Hutton | 600/219 |
| 2007/0156025 A1 | 7/2007 | Marchek et al. | |
| 2007/0161867 A1 * | 7/2007 | Fowler et al. | 600/233 |
| 2007/0203399 A1 | 8/2007 | Gephart et al. | |
| 2007/0208228 A1 * | 9/2007 | Pavento et al. | 600/233 |
| 2007/0238932 A1 | 10/2007 | Jones et al. | |
| 2007/0282171 A1 | 12/2007 | Karpowicz et al. | |
| 2009/0069635 A1 | 3/2009 | Gephart et al. | |

FOREIGN PATENT DOCUMENTS

| | | |
|---|---|---|
| WO | 2004047650 | 10/2004 |
| WO | 2005092206 | 6/2005 |
| WO | 2005094695 | 10/2005 |
| WO | 2005096735 | 10/2005 |
| WO | 2007087536 | 8/2007 |

OTHER PUBLICATIONS

Amendment filed Apr. 14, 2010, in U.S. Appl. No. 11/539,224 (25 pages).

United States Patent and Trademark Office, Final Office Action mailed Jul. 7, 2010 in U.S. Appl. No. 11/539,224 (15 pages).

Amendment filed Dec. 6, 2010, in U.S. Appl. No. 11/539,224 (14 pages).

Syn Frame Access and Retractor System Assembly guide, SYNTHES Spine, assembly guide provided by the manufacturer, 1999, 12 pages, Paoli, Pennsylvania.

ProAccess Radiolucent Retractor Blades, SYNTHES Spine, product offerings guide provided by the manufacturer, 2004, 2 pages, Paoli, Pennsylvania.

Weeb, J., Spine—the future, AO foundation Webpage, available at:http://www.aofoundation.org/AOFileServer/PortalFiles?FilesPath=/Extranet2007/active/_att/wor/actDialogue/1999_2/spine.pdf, accessed Apr. 10, 2009.

* cited by examiner

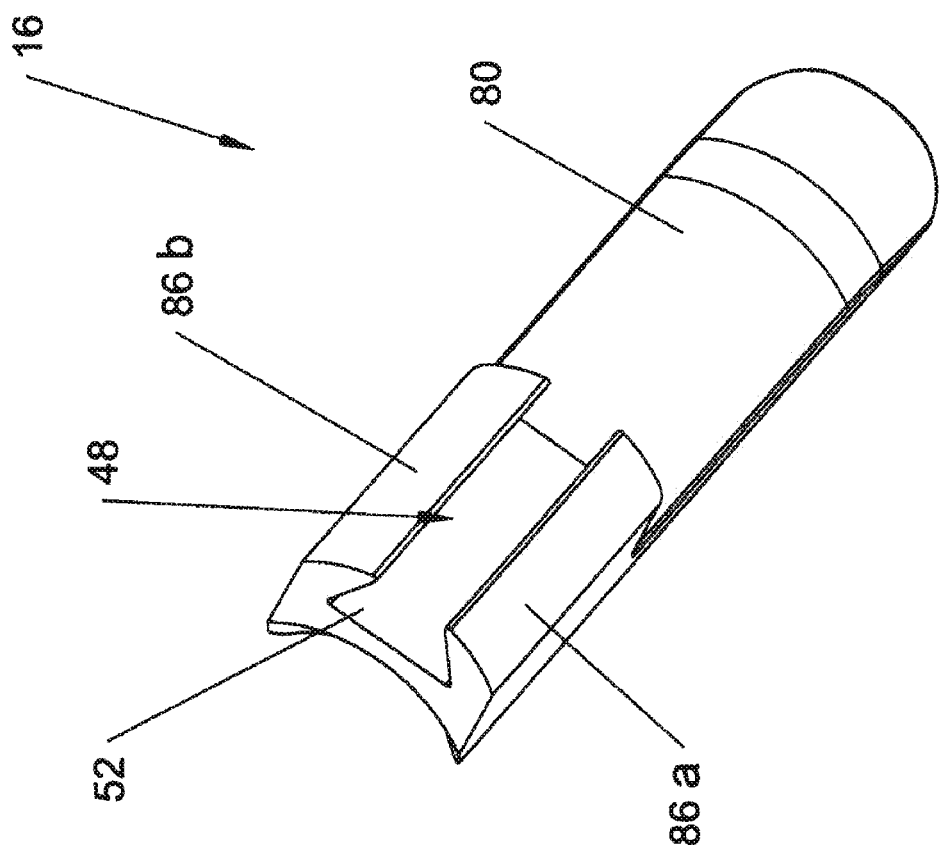
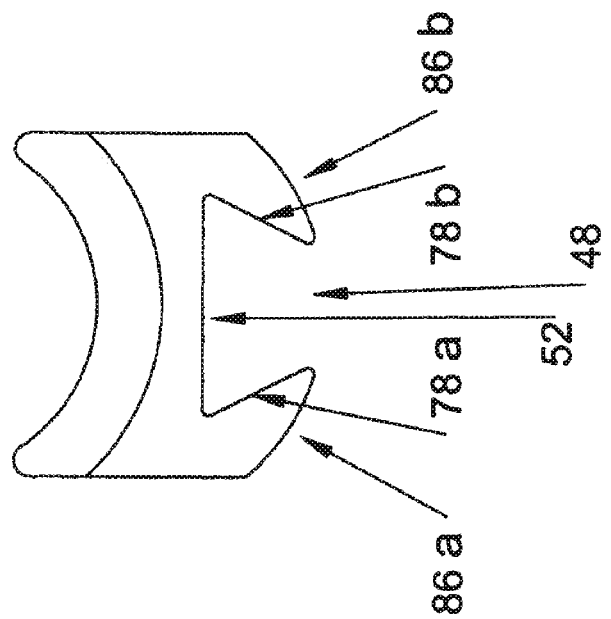
FIG. 10 A
FIG. 10 B

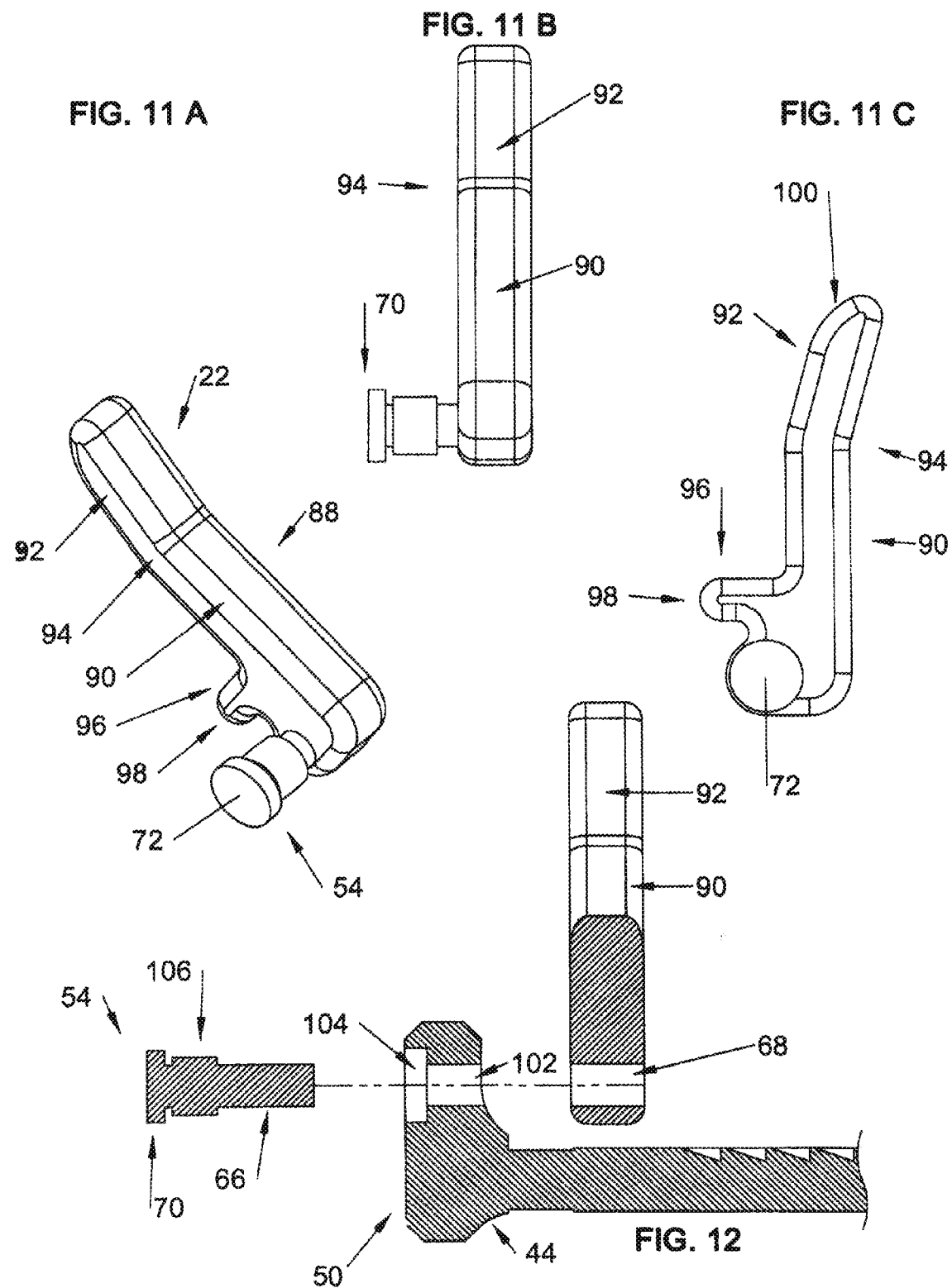

RETRACTION APPARATUS AND METHOD OF USE

CROSS-REFERENCE TO RELATED APPLICATION

This application claims the benefit of U.S. Provisional Patent Application Ser. No. 61/057,639, filed May 30, 2008, which is hereby incorporated by reference as if fully set forth herein.

FIELD OF THE INVENTION

The invention relates generally to a retractor and method for providing access to a surgical site and, more particularly, a retractor and method for retracting tissue during a surgical procedure.

BACKGROUND OF THE INVENTION

Surgical retractors are devices that utilize tissue engaging members, such as retractor blades, to increase the size of an incision and provide access to a surgical site. Retractors permit a surgeon to retract soft tissues surrounding the incision and obtain a clear view of the operating site during a procedure. By retracting the tissue surrounding the incision to form an enlarged surgical channel, a relatively small incision may be used which minimizes trauma to the patient and shortens recovery time. However, existing surgical retractors continue to suffer from a number of shortcomings which make them difficult to use.

One such problem is the ability to easily adjust the depth of the retractor blades within an incision to avoid striking bones when the blades retract. A number of prior retractors attempt to solve this problem by providing upward and downward adjustment of the retractor blades. However, these systems are difficult to adjust and require tools to manipulate the position of the retractor blades. For example, U.S. Patent Application Publication No. 2007/0238932 to Jones et al. discloses a locking mechanism having a worm gear which adjusts the position of an associated retractor blade. The engagement between the worm gear and the retractor blade is under a high torque to inhibit unintentional movement of the retractor blade. To overcome this high torque and adjust the retractor blade position, a user inserts an elongate tool into the locking mechanism and rotates the tool about its longitudinal axis. As is apparent, this approach is time-consuming and requires a significant amount of tool rotation to individually adjust the retractor blades. Thus, a need exists for a retraction apparatus that is easier to use.

Another problem with existing surgical retractors is the difficulty involved with connecting or removing retractor blades. For example, U.S. Patent Application Publication No. 2007/0203399 to Gephart et al. discloses connecting a retractor blade to a retractor slider by biasing a locking pin against the retractor blade. Once the locking pin is aligned with one of a plurality of holes in the retractor blade, the locking pin projects into the hole to retain the retractor blade on the slider. To remove the retractor blade from the slider, an unlocking instrument is inserted into the retractor blade hole to push the locking pin out of engagement therewith. Similarly, the locking pin must also be pushed out of engagement before the retractor blade can be adjusted to a different depth within the incision. This approach is clearly problematic, as having to use an instrument to adjust or remove each retractor blade unduly prolongs surgery. Further, the plurality of holes in the retractor blade restricts the blade to a discrete number of positions along the slider, which limits the ability of a surgeon to adjust the blade depth to conform to a patient's anatomy. Therefore, a need exists for a retractor that permits removal and flexible adjustment of the retractor blades without the use of an additional tool.

Retracting soft tissue in close proximity to a bone poses yet another problem for standard surgical retractors because the retractor blades cannot retract the tissue toward the bone to position the surgical channel near the bone. For example, the U.S. Patent Application Publication to Jones et al. discussed above discloses a D-shaped retractor frame with a straight side that is aligned along a length of the spine. Support structures carry the retractor blades between unretracted and retracted positions, with the support structure of the straight side retracting along a path perpendicular to the straight side itself. With the retractor blades in the retracted position, the thickness of the straight side retractor blade and its connection to the support structure limit how far the surrounding tissue can be retracted toward the bone. Also, if the bone is elevated above the surrounding anatomy, the straight side support structure may strike the bone, which limits the size of the enlarged opening. Accordingly, an access retractor that may be placed adjacent a bone and used to enlarge an incision toward the bone without being limited by a retractor blade or its support structure would be desirable.

SUMMARY OF THE INVENTION

In accordance with one aspect of the invention, a retraction apparatus is provided having a locking mechanism for locking a tissue engagement member, such as retractor blade, to a slider member at a selected depth in an incision. The locking mechanism has a pivot lever that is pivotal between an unlocked position that allows the retractor blade to be slidably adjusted upwardly or downwardly and a locked position that fixes the retractor blade at the selected depth. As is apparent, rather than having to depress spring-loaded pins or rotate worm gears to adjust the retractor blade, the pivot lever permits the retractor blade to be easily and rapidly positioned at a desired depth within an incision and fixed thereat with a simple pivoting motion. Further, utilizing a pivot lever to control the movement of the retractor blade provides an intuitive manner of locking the retractor blade that is simple to use.

In one form, pivoting the pivot lever to the locked position creates a frictional engagement between the slider member and the retractor blade that fixes the slider member and the retractor blade together. This frictional engagement avoids reliance on complicated mechanical interfaces that may become fouled during surgery. The locking mechanism may also include a locking member that is preferably flush with an end of the slider member when the pivot lever is in the unlocked position. Before the pivot lever is pivoted to the locked position, the retractor blade may be slidably mounted onto the slider member and positioned at the desired depth within the incision. Pivoting the pivot lever presses the locking member against a contact surface of the retractor blade and shifts the retractor blade against the slider member to fix the retractor blade at the desired depth within the incision. Preferably, the slider member and the retractor blade have a slide connection therebetween that permits the retractor blade to slide upwardly and downwardly relative to the slider member. With the pivot lever in the unlocked position, the retractor blade can be positioned at an infinite number of positions along the connection to conform the blade closely to the anatomy of a patient.

In accordance with another aspect of the invention, a retraction apparatus is provided having a cantilever lock between a slider member and a retractor blade. The cantilever lock pivots the retractor blade relative to the slider member to rigidly fix the retractor blade at a selected depth within the incision. Unlike prior locking mechanisms, the cantilever lock fixes the retractor blade to the slider member by shifting a portion of the retractor blade away from the slider member while pressing another portion of the retractor blade against the slider member. Such an operation permits the retractor blade to be rapidly connected to the slider member, adjusted to the selected depth, and fixed to the slider member. Removing or repositioning the retractor blades is also straightforward, as the retractor blade need only be released from engagement against the slider member. The cantilever lock preferably employs a locking member connected to the slider member that is advanceable beyond a slider member end portion and into contact with a retractor blade locking surface. The locking member shifts an upper portion of the retractor blade locking surface away from the slider member, which presses a lower portion of the locking surface tightly against the slider member end portion to fix the retractor blade against the slider member.

The cantilever lock may have several other features that operate to fix the retractor blade to the slider member. For instance, the cantilever lock may include a clamping lever that is pivotal between an unlocked position which allows the retractor blade to be adjusted to a selected depth in the incision, and a locked position which fixes the retractor blade at the selected depth. In one form, the retractor has a slide connection between the retractor blade and the slider member so that the retractor blade slides along a slider member end portion and can be positioned at the selected depth in the incision. Once the retractor blade is in position, the locking member connected to the slider member end portion advances into contact with the retractor blade to shift the retractor blade against the slider member end portion. Shifting the retractor blade removes substantially all of the play within the slide connection and rigidly fixes the retractor blade to the slider member. Further, another adaptation of the cantilever lock uses the locking member to shift an upper end of the retractor blade away from the slider member, which pivots a lower end of the blade in an opposite direction.

In another aspect of the invention, a retraction apparatus is provided having a retractor body straight portion with a substantially flat surface configured to be placed adjacent a bone. A pair of opposed retractor body portions are connected at either end of the straight portion and extend transversely to the straight portion. This way, slider members received within the opposed portions retract in directions transverse to the straight portion and avoid striking the bone. If the bone is relatively narrow, the retractor blades may retract to a position wider than the bone such that the retractor blades and retracted soft tissues are positioned on opposing sides the bone. Soft tissue retracted by the blades is relatively taught, so positioning the blades on opposing sides of the bone stretches the soft tissue against the bone and widens the operating channel toward the bone.

The retractor body preferably has a bridge portion that extends between the opposed retractor body portions and orients them at an incline relative to each other. The incline produces a V-shape between the opposed retractor body portions and positions the slider members at an angle relative to one another. Unlike prior configurations with retractor blades that retract in opposite directions along a shared axis, the transverse paths of the slider members permit both slider members to retract in a similar direction, such as toward a bone adjacent the retractor body. This configuration is desirable, as a pair of retractor blades retracting toward the bone tends to position the surgical channel closer to the bone than would a single retractor blade retracting toward the bone.

In some instances, it is desirable to have a minimum number of blades to improve operability in tight working environments. To this end, the retractor apparatus may employ a third slider member that retracts in a direction transverse to the paths of the other slider members so that the size of the incision may be maximized using only three retractor blades. Specifically, with the flat surface of the retractor body straight portion positioned adjacent a bone, the pair of retractor blades associated with the opposed retractor body portions retract tissue toward either side of the bone. The third slider member is disposed in the retractor body bridge portion such that the connected retractor blade retracts soft tissue away from the bone. Thus, the soft tissue is retracted toward either side of the bone as well as away from the bone to maximize the retracted incision opening with only three retractor blades.

Another feature of the retractor body is that the pair of opposed retractor body portions may be pivotal relative to the straight portion about transverse pivot axes. Pivoting the retractor body portions upward "toes out" the ends of the retractor blades so that there is greater room to operate deeper within the incision. Further, when the flat surface of the retractor body straight portion is positioned adjacent a bone, toeing out the retractor blades may press soft tissue against the bone to create even greater room within the incision.

A method of connecting a retractor blade to a slider member is also provided and includes mounting the retractor blade to the slider member and pivoting a clamping lever between unlocked and locked positions. With the clamping lever in the unlocked position, the retractor blade can be slidably adjusted upwardly or downwardly to a selected depth in an incision. Pivoting the clamping lever to the locked position restricts movement of the retractor blade. The method also includes pivoting the retractor blade relative to the slider member which tightly presses the retractor blade against the slider member and fixes the retractor blade to the slider member at the selected depth in the incision.

BRIEF DESCRIPTION OF THE DRAWINGS

FIG. 10A is a perspective view of a retractor blade showing the locking surface of the retractor blade;

FIG. 10B is a top plan view of the retractor blade of FIG. 10A showing the retractor blade having a dovetail recess for connecting to the dovetail projection of the slider assembly;

FIGS. 11A-11C are a series of views of the handle connected to the wedge pin which show a contact surface of the wedge pin;

FIG. 12 is an exploded cross-sectional view of the wedge pin, slider assembly end portion, and handle showing a shaft of the wedge pin aligned with a bore of the end portion and a bore of the handle;

DETAILED DESCRIPTION OF THE PREFERRED EMBODIMENTS

Figure 1:
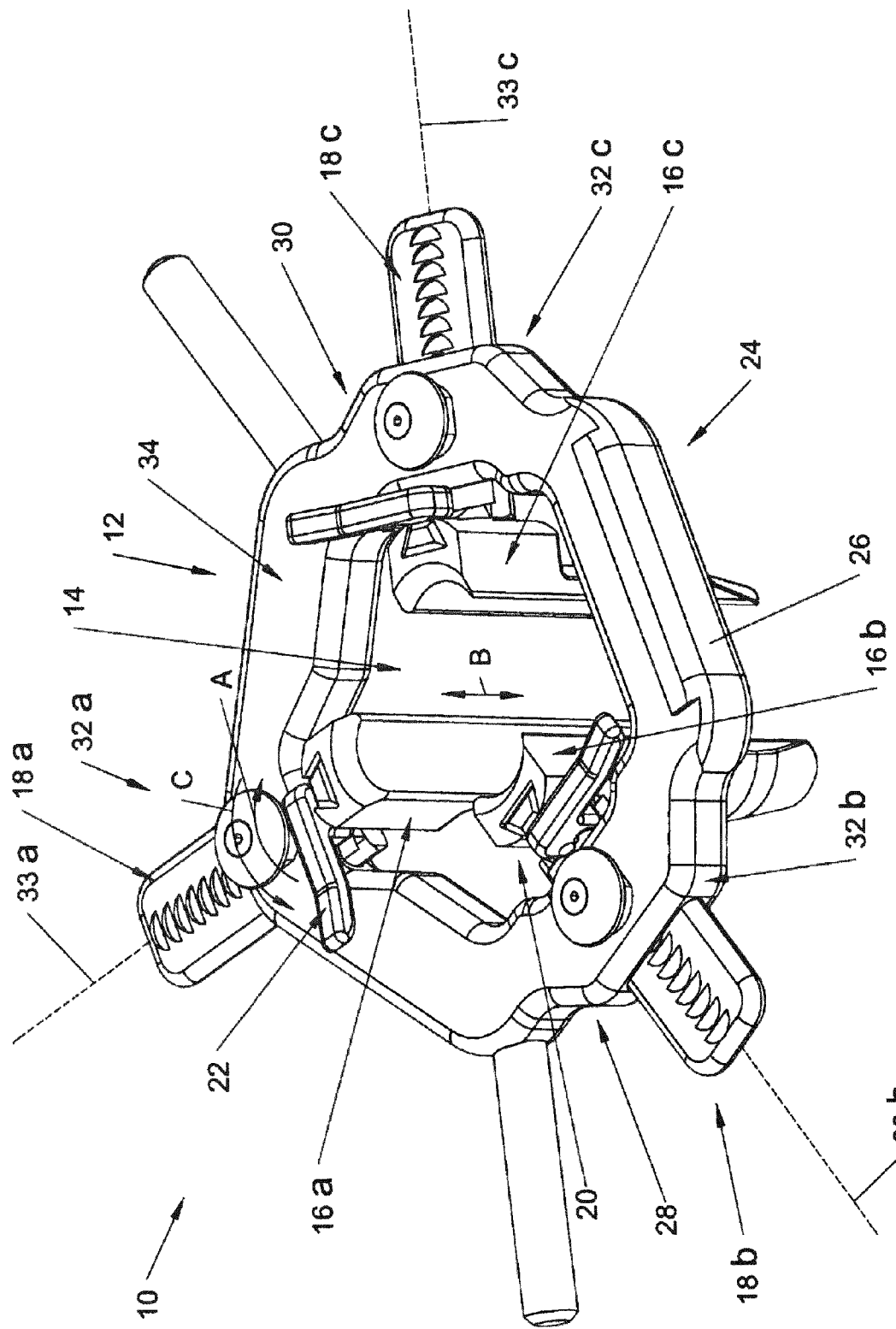
FIG. 1 is a perspective view of an access retractor in accordance with the present invention showing slider assemblies having handles in a locked position and retractor blades fixed to the slider assemblies.

Referring initially to FIG. 1, an access retractor 10 in accordance with the present invention is depicted in a representative embodiment and set up with the apparatus 10 including a frame or body 12 with a large retraction opening 14 centrally located for accessing a surgical site. Inside the opening 14 are located a number of tissue engaging members, such as in the form of retractor blades 16a, 16b, and 16c, which are used to expand an incision and are shown in a fully retracted position. Slider assemblies 18a, 18b, 18c are slidably mounted to the retractor body 12 and connect the blades 16 thereto.

Preferably, each slider assembly 18 has a locking mechanism 20 for fixing the blade 16 to the slider assembly 18. The locking mechanism 20 includes a pivot or clamping lever, such as a handle 22, which may be pivoted in direction A to an unlocked position that allows the blade 16 to be connected or removed relative to the slider assembly 18. When the handle 22 is in the unlocked position, the blade 16 may also be adjusted upwardly and downwardly to a desired depth within the incision, as indicated by arrow B. Then, the handle 22 is pivoted in direction C to the locked position shown in FIG. 1 which fixes the blade 16 at the selected depth in the incision. In one form, the locking mechanism 20 employs a cantilever lock that pivots the blade 16 relative to the slider assembly 18 to fix blade 16 to the slider assembly 18.

The retractor 10 may also include several features which improve the ability of a surgeon to retract soft tissue when the retractor 10 is positioned near a bone. More specifically, the retractor body 12 has a straight portion 24 with a flat surface 26 that is configured to be placed adjacent a bone. A pair of opposed retractor body portions 28, 30 are connected at either end of the generally straight portion 24 and extend transversely to the straight portion 24. The opposed body portions 28, 30 have slide connections 32b, 32c that connect the slider assemblies 18b, 18c to the retractor body 12 and position the slider assemblies 18b, 18c at angles relative to the straight portion 24. In this manner, the slider assemblies 18b, 18c advance and retract along axes 33b, 33c and avoid contact with the bone adjacent the straight portion 24.

Figure 2:
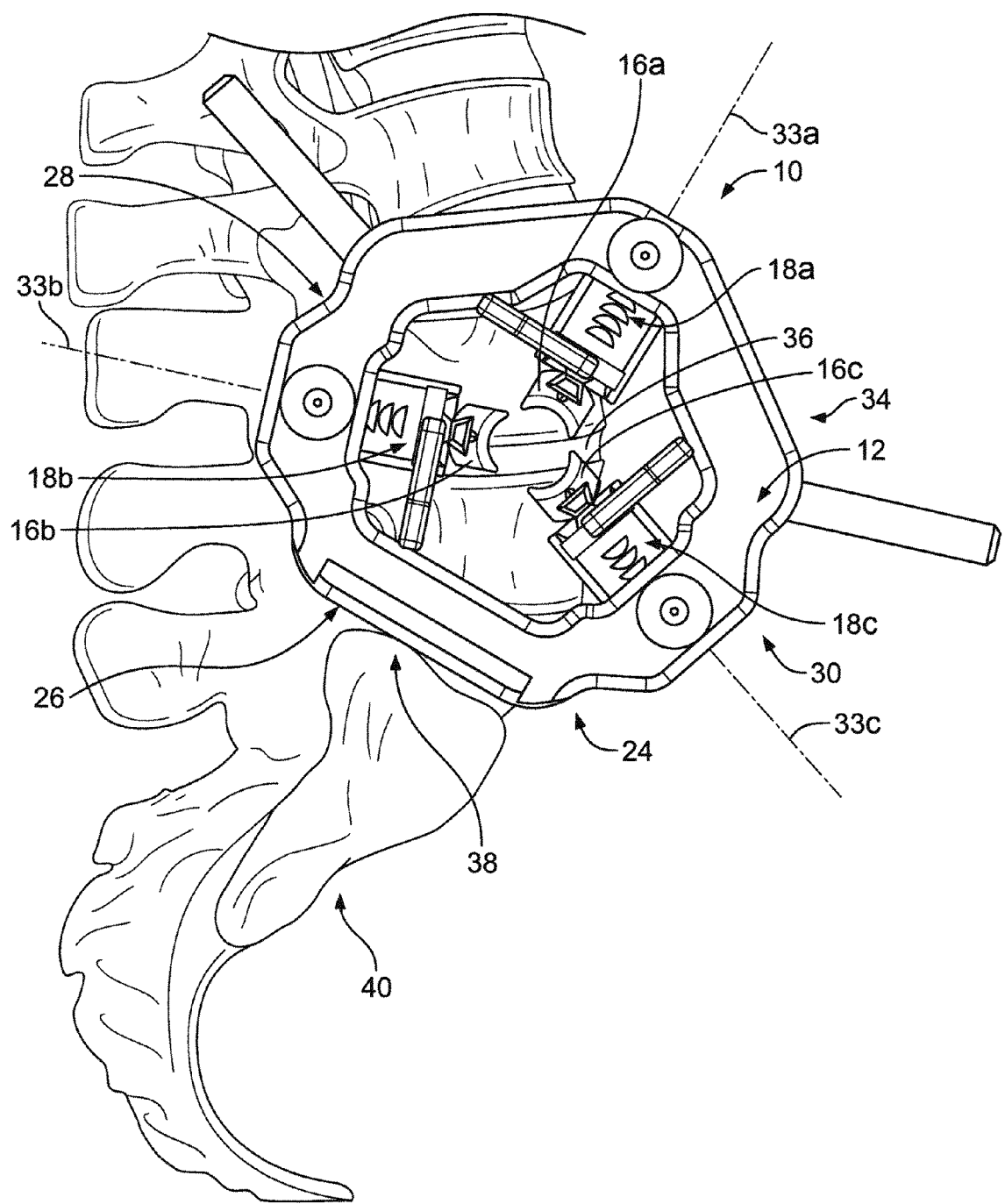
FIG. 2 is a top view of the access retractor of FIG. 1 positioned on a human spine to illustrate a lateral approach surgical procedure wherein a substantially flat surface of the access retractor abuts the iliac crest of the pelvis.
Figure 3:
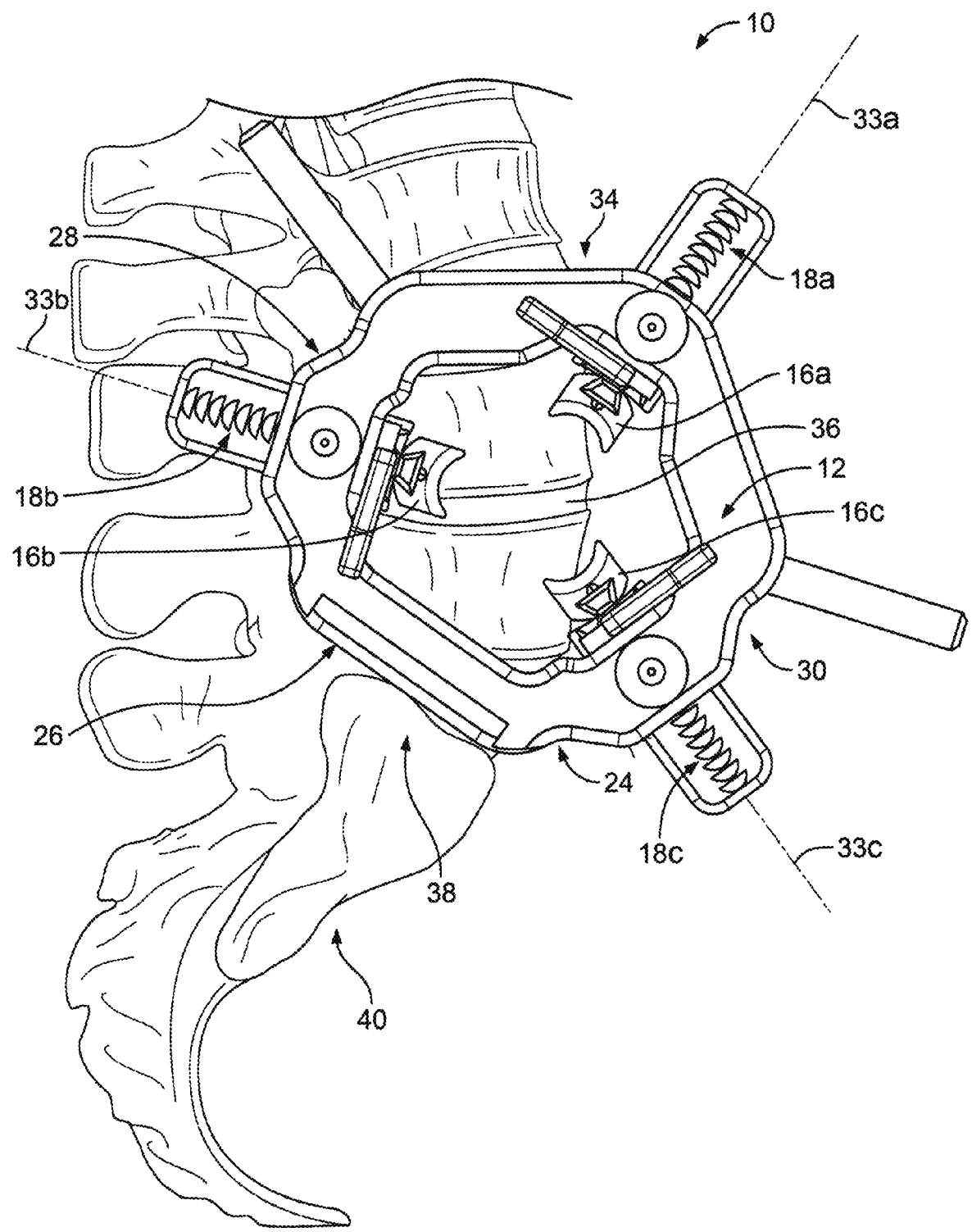
FIG. 3 is a top view of the access retractor and spine of FIG. 2 showing the slider assemblies retracting without striking the iliac crest and how soft tissue is generally retracted to opposing sides of the iliac crest.

An exemplary application of the access retractor 10 is shown in FIGS. 2 and 3, wherein the retractor 10 is being used to provide lateral access to an intervertebral disc 36 between L4 and L5 vertebra. In the approach shown, the flat surface 26 is placed against the iliac crest 38 (which projects out of the page) and the blades 16 are positioned above the intervertebral disc 36 in their unretracted position. Moving between FIGS. 2 and 3 illustrates the transition of the slider assemblies 18a, 18b, and 18c and connected blades 16a, 16b, and 16c to their retracted positions. As is apparent, the blades 16b, 16c are capable of expanding tissue (not shown) away from the intervertebral disc 36 and toward the iliac crest 38 without the slider assemblies 18b, 18c striking the iliac crest 38. In another application, a substantially flat lower surface of the straight portion 24 is positioned in overlapping relation with a portion of the pelvis 40. This way, the retractor blades 16b, 16c are positioned on either side of the iliac crest 38 in their retracted positions, which stretches the tissue across the iliac crest 38. The tissue extending between the blades 16b, 16c is relatively taught, so positioning the blades on opposing sides of the iliac crest 38 stretches the tissue against the pelvis 40 and widens the operating channel toward the pelvis 40. In either application, a surgical channel is formed near the pelvis 40 without any of the blades 16 retracting against the pelvis 40, as was commonplace with prior retractors.

The retractor body 12 may include a bridge portion 34 extending between opposed retractor body portions 28, 30, as shown in FIG. 1. The bridge portion 34 is preferably wider than the straight portion 24 to orient the opposed body portions 28, 30 at an incline relative to each other so that the slider assemblies 18b, 18c retract in directions transverse to one another. A third slider assembly 18a is connected to the bridge portion 34 at slide connection 32a and retracts along an axis 33a that is perpendicular to the retractor body straight portion 24. By retracting the blade 16a away from the straight portion 24, the slider assembly 18a expands the surgical channel positioned near the bone by the slider assemblies 18b, 18c. In this manner, the incision can be expanded using only three slider assemblies 18a, 18b, and 18c. However, access retractor 10 may be configured to utilize more than three slider assemblies 18, and the slider assemblies 18 may be configured to be used with different access retractors.

Figure 4:
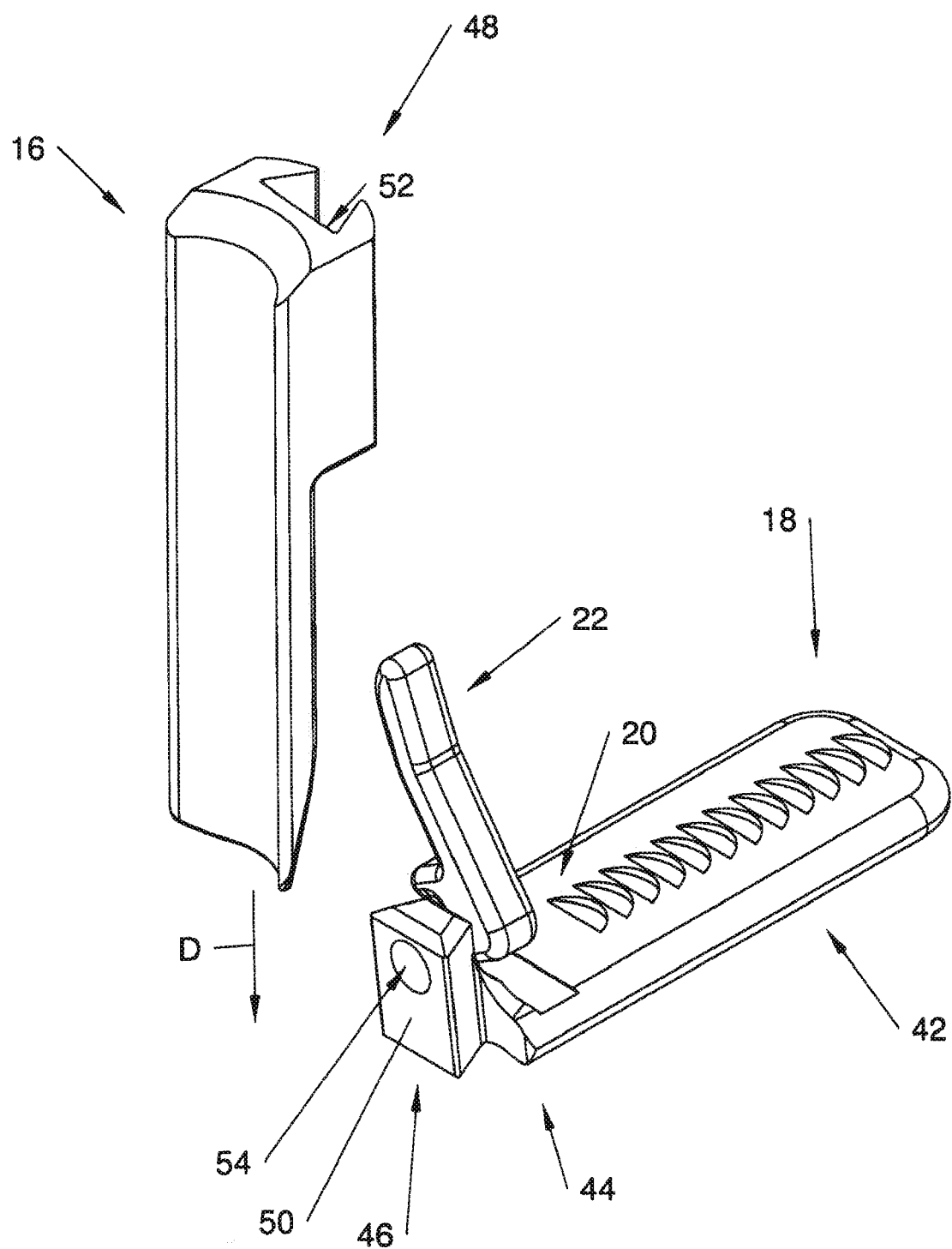
FIG. 4 is a perspective view of a slider assembly and a retractor blade showing the manner of connecting the retractor blade to an end portion of the slider assembly.
Figure 5:
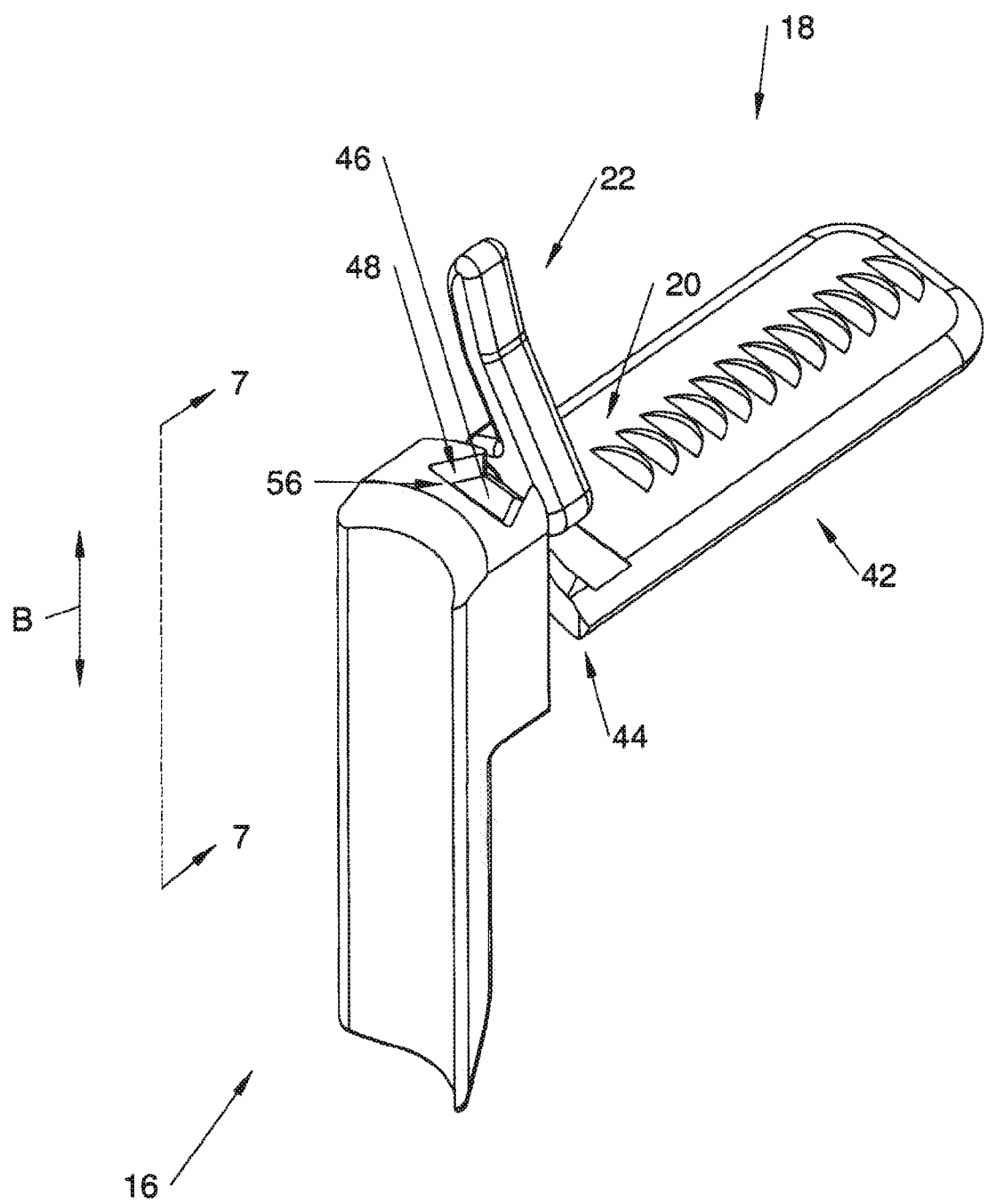
FIG. 5 is a perspective view of the slider assembly and retractor blade of FIG. 4 showing the retractor blade slidably mounted to the slider assembly end portion with the handle in an unlocked position.
Figure 6:
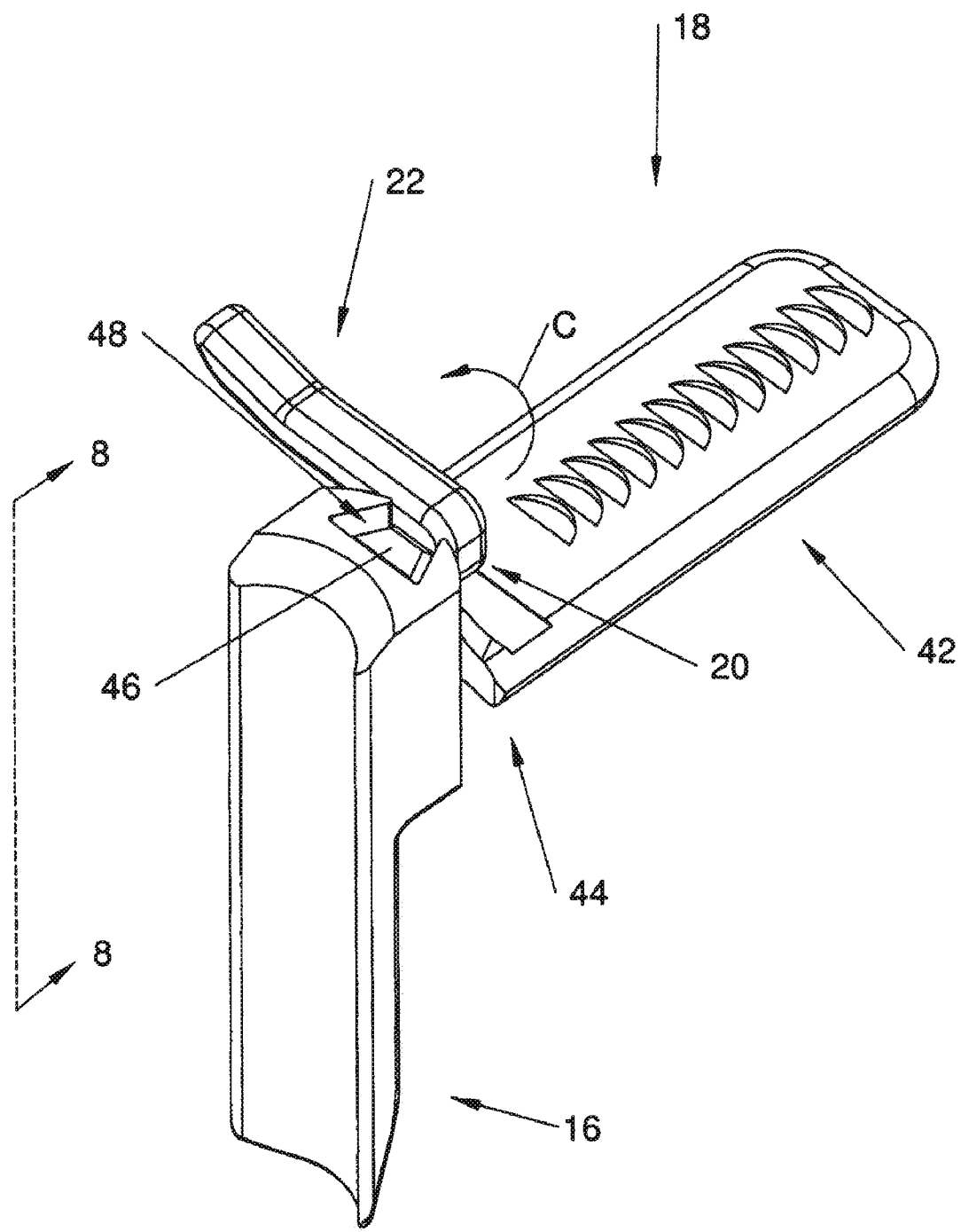
FIG. 6 is a perspective view of the slider assembly and retractor blade of FIG. 5 showing the handle pivoted to the locked position which fixes the retractor blade to the slider assembly.

Turning to FIGS. 4-6, the process of fixing retractor blade 16 to slider assembly 18 is illustrated in greater detail. The slider assembly 18 includes a ratcheting slider 42 having an end portion 44 for connecting to the retractor blade 16. In a preferred form, the end portion 44 has a dovetail projection 46 that engages a corresponding dovetail recess 48 on the retractor blade 16. Additionally, the end portion 44 has a confronting surface 50 that abuts a locking surface 52 of the blade 16 when the blade 16 is connected to the end portion 44. It is appreciated that the end portion 44 may include any number of connection types, including hooks, tongue in grooves, ball joints, or more complex mechanical devices, such as ratcheting or gear-based interfaces.

The locking mechanism 20 may include a locking member, such as a wedge pin 54, which is configured to press against the blade locking surface 52 to fix the blade 16 to the slider assembly 18. In a preferred form, the wedge pin 54 is flush with the confronting surface 50 when the handle 22 is in the unlocked configuration, as shown in FIG. 4. This minimizes interference during installation of the blade 16 onto the end portion 44, though alternative configurations may have the wedge pin 54 recessed within the confronting surface 50 or projecting outward therefrom.

To mount or connect the blade 16 to the slider assembly 18, the dovetail recess 48 is aligned with the dovetail projection 46 and the blade 16 is moved in direction D relative to the slider assembly 18 to position the dovetail recess 48 onto the dovetail projection 46. As shown in FIG. 5, the resulting connection between the blade 16 and the slider assembly 18 is a slide connection 56 such that the blade 16 may translate upwardly or downwardly generally parallel to arrow B with the handle 22 in the unlocked position. Further, the slide connection 56 includes a continuous bearing surface, such as the slider assembly confronting surface 50, which permits infinite variability of the blade 16 position therealong. The slide connection 56 preferably limits the blade 16 to translational movement along the end portion 44 and may restrict the blade 16 from passing completely beyond the end portion 44. In the embodiment shown, the dovetail recess 48 and the dovetail projection 44 form the slide connection 56 between the blade 16 and the slider assembly 18. However, it is appreciated that a number of different interfaces will provide the translational movement of the blade 16.

Once the blade 16 is positioned at the desired depth in the incision, the handle 22 is pivoted in direction C to the locked position to fix the blade 16 to the slider assembly 18, as shown in FIG. 6. With the handle 22 in the locked position, the locking mechanism 20 restricts the blade 16 from moving relative to the slider assembly 18. Further, pivoting the handle 22 from the unlocked to locked position eliminates the translational freedom of motion of blade 16 relative to the slider assembly 18 as represented by arrow B in FIG. 5.

Figure 7:
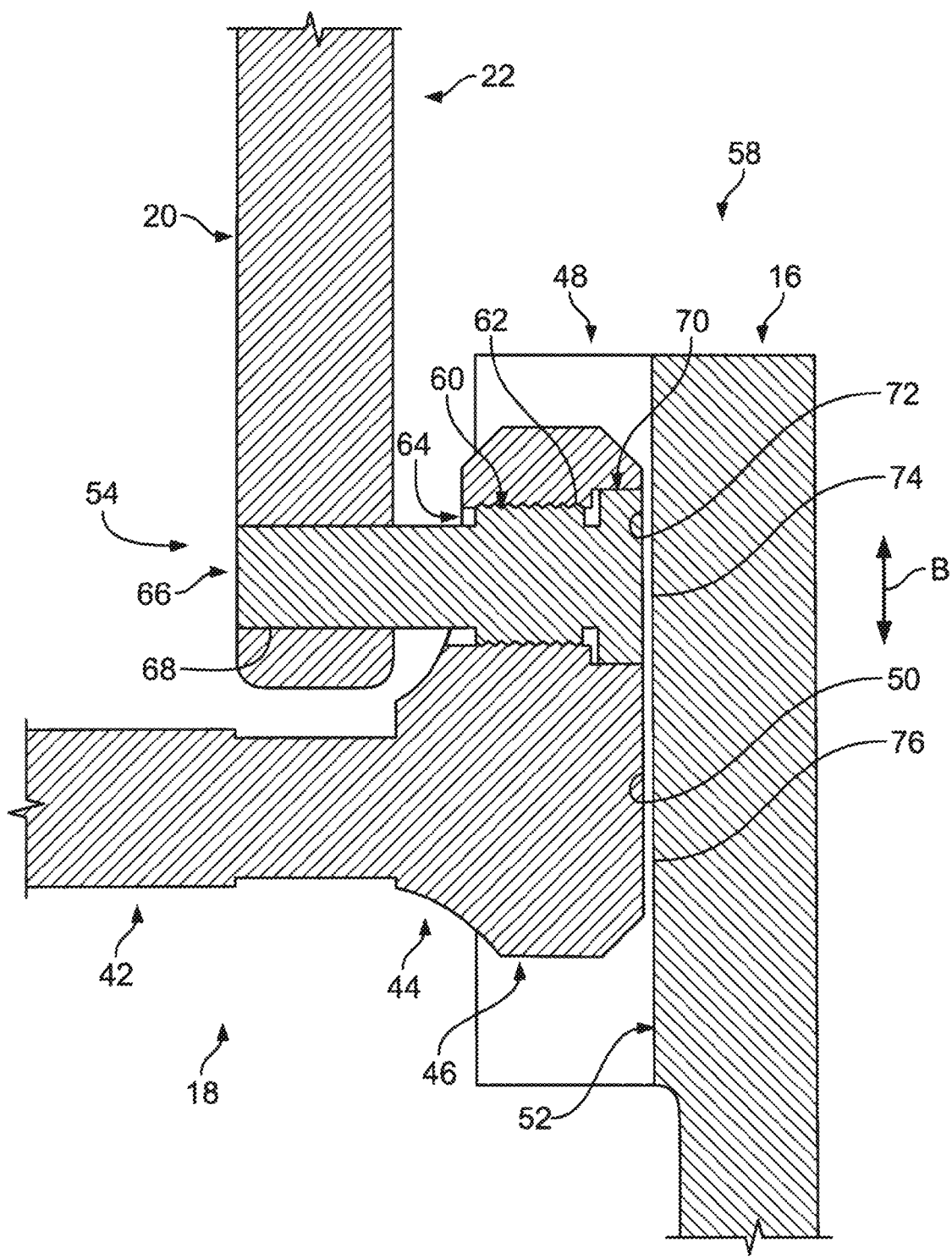
FIG. 7 is a cross sectional view taken across line 7-7 in FIG. 5 showing one embodiment of a slider assembly locking mechanism with the handle in the unlocked position such that the retractor blade may be slidably adjusted upwardly or downwardly.
Figure 8:
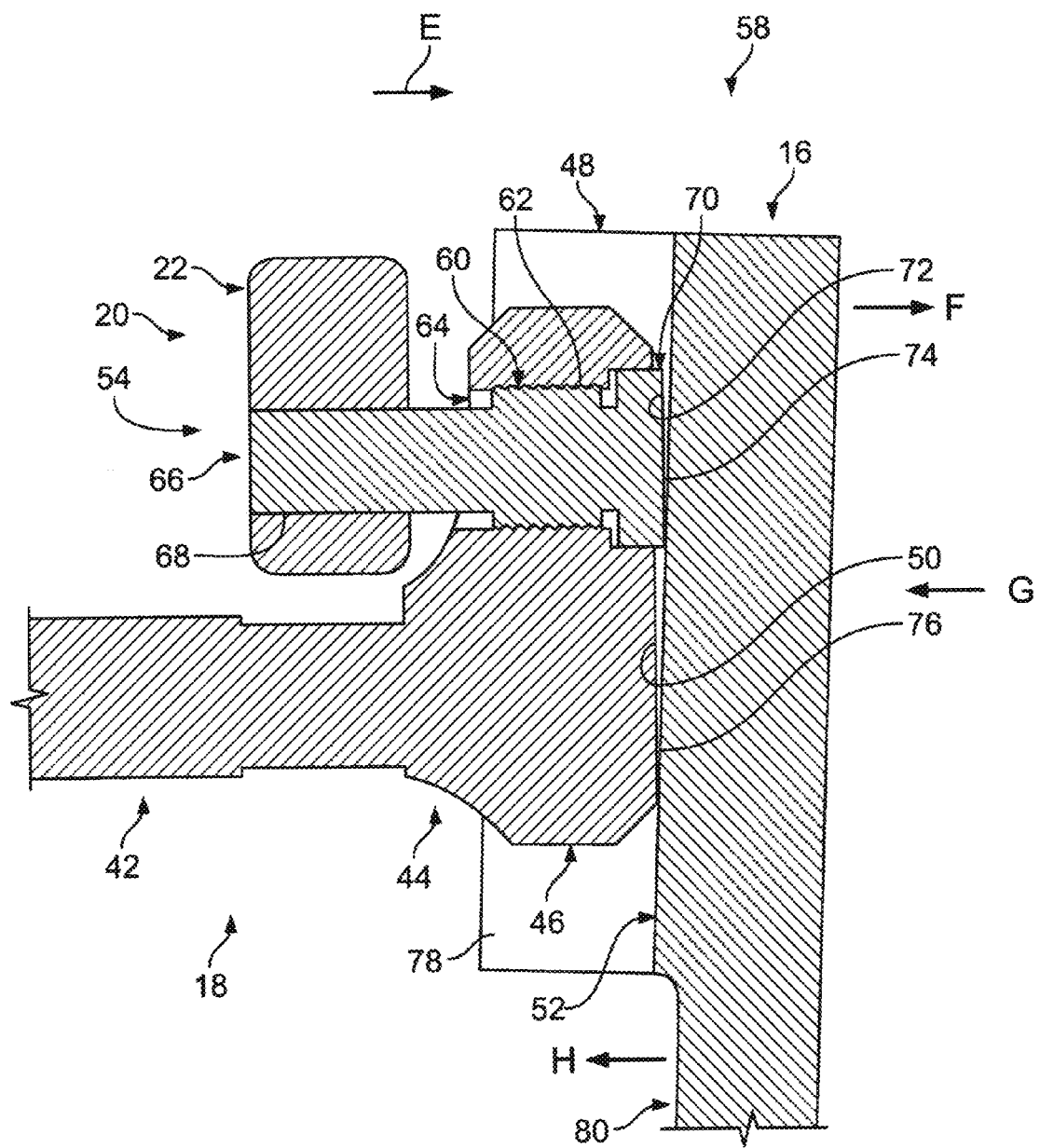
FIG. 8 is a cross sectional view taken across line 8-8 in FIG. 6 showing the handle pivoted to the locked position which presses a wedge pin against a retractor blade locking surface to shift an upper portion of the locking surface away from the slider assembly end portion and press a lower portion of the locking surface against the end portion.

In one embodiment, the locking mechanism 20 has the form of a cantilever lock 58 that engages the blade 16 to the slider assembly end portion 44 by pivoting the blade 16 relative to the slider assembly 18, as shown in FIGS. 7 and 8. FIG. 7 illustrates the cantilever lock 58 in the unlocked position, wherein the handle 22 is generally oriented along the plane of the page and the blade 16 may translate upwardly and downwardly as represented by arrow B. To pivot the blade 16, the locking mechanism 20 preferably includes a fastener, such as wedge pin 54, having a head portion 70 with a contact surface 72 that is pressed against the blade locking surface 52 to pivot the blade 16. Preferably, both the locking surface 52 and the contact surface 72 are substantially flat to provide a simple engagement that resists jamming, though the surfaces 52, 72 may have projections, recesses, or other features.

The locking surface 52 has an upper portion 74 and a lower portion 76, and the wedge pin 54 presses against the upper portion 74. In one form, the wedge pin 54 is a threaded fastener with a threaded portion 60 that engages threads 62 of a slider assembly bore 64. A wedge pin shaft 66 is connected to the handle 22 such that pivoting the handle 22 advances and retracts the wedge pin 54 and the handle 22 along the ratcheting slider 42, as generally indicated by arrow E in FIG. 8. Moreover, pivoting the handle 22 into the locked position presses the contact surface 72 of the wedge pin 54 against the locking surface upper portion 74 and shifts the blade 18 in direction F.

As the locking surface upper portion 74 shifts away from the slider assembly end portion 44, the cantilever lock 58 pivots the locking surface lower portion 76 in direction G tightly against the slider assembly confronting surface 50 which tightly fixes the blade 16 to the slider assembly end portion 44. The frictional engagement between the locking surface lower portion 76 and the confronting surface 50 acts as a frictional lock which locks the retractor blade 16 to the slider assembly end portion 44. Further, pivoting the handle 22 presses the wedge pin 54 against the retractor blade 16 and produces tactile feedback such that the handle 22 becomes more difficult to pivot as the wedge pin 54 tightly engages the retractor blade 16 against the slider member 18.

When the wedge pin 54 presses the locking surface lower portion 76 against the slider assembly confronting surface 50, the wedge pin 54 removes all of the play or slop from the slide connection 56 and rigidly fixes the retractor blade 16 to the slider assembly end portion 44. In the preferred form, shifting the blade 16 in direction F also tightly presses inclined surfaces 78 of the dovetail recess 48 against corresponding surfaces of the dovetail projection 46. This engagement restricts movement of blade 16 in direction F and further fixes the blade 16 to the slider assembly 18. Additionally, shifting locking surface upper portion 74 in direction F causes a lower, outer blade surface 80 which faces the retracted tissue to shift in direction H and further expand the operating channel.

It is appreciated that locking mechanism 20 may have alternative configurations which lock the blade 16 to the slider assembly 18. For example, a variation of the cantilever lock 58 may include a mechanical drive, ratchet, or even pneumatics to advance the wedge pin 54 against the blade 16 instead of a pivotal handle 22. Another variation of the locking mechanism 20 may include a linkage that transmits movement of the handle 22 to fix the blade 16 relative to the slider assembly 18.

Figure 9:
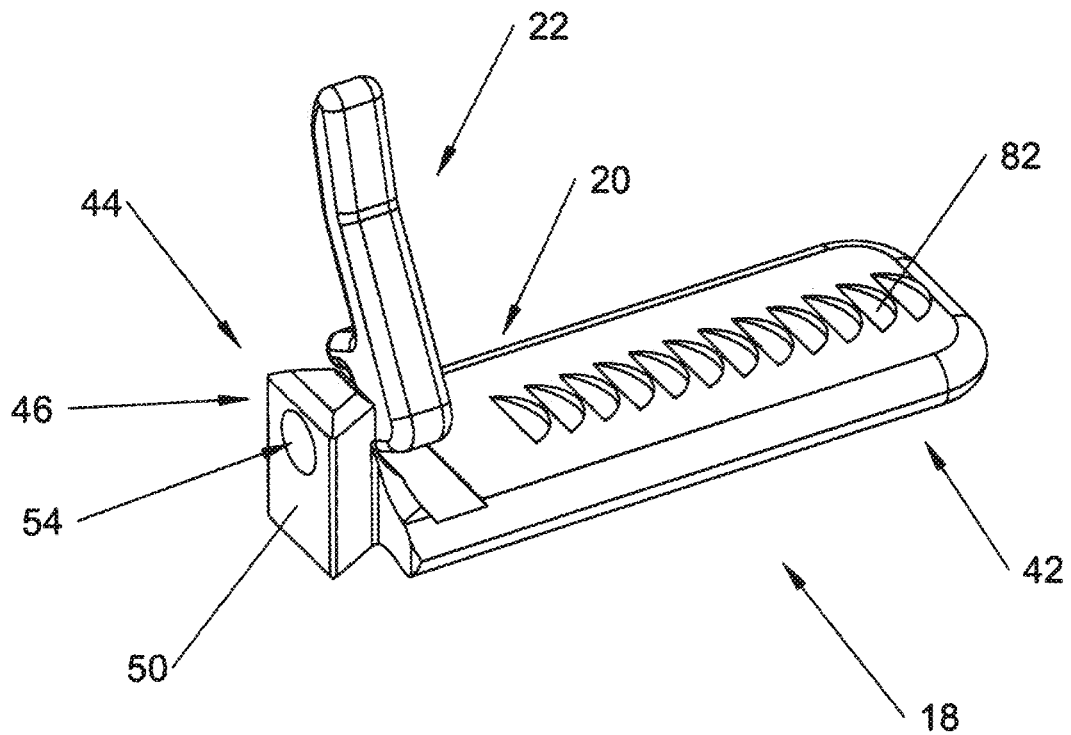
FIG. 9A is a perspective view of the slider assembly showing the wedge pin received within the slider assembly end portion.
FIG. 9B is a top plan view of the slider assembly of FIG. 9A showing the end portion having a dovetail projection.
Figure 9:
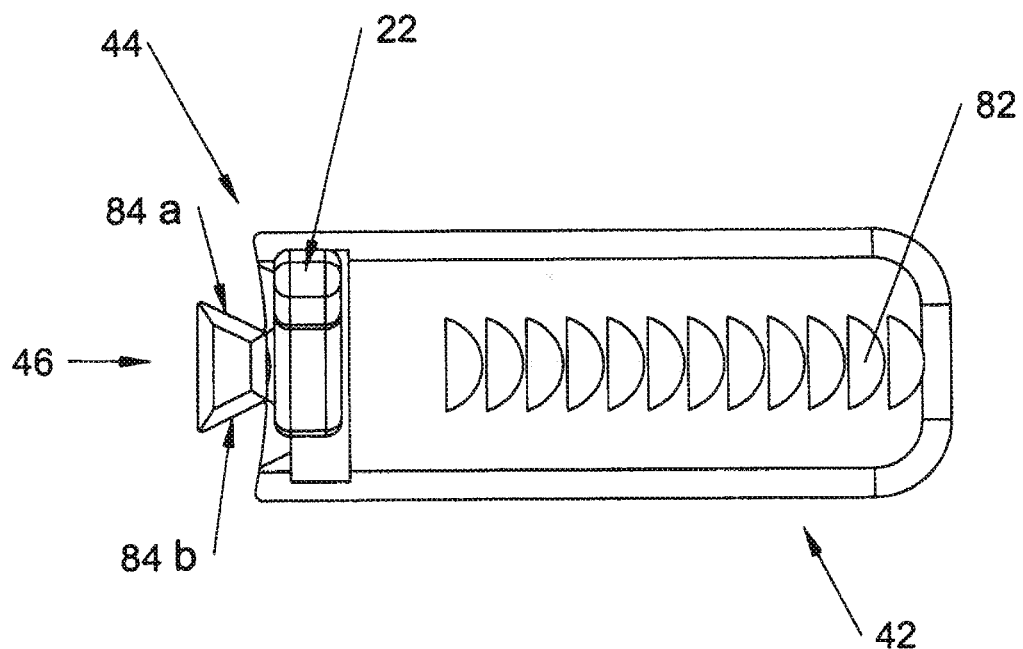

Turning now to the specifics of the slider assembly 18, the ratcheting slider 42 includes ratchet teeth 82 that engage the slide connection 32 and permit a surgeon to selectively position the associated blade 16 at a predetermined position within the opening 14, as shown in FIG. 9A. The ratcheting slider 42 is relatively elongate, with an end portion 44 preferably having a dovetail projection 46 with a confronting surface 50 and a wedge pin 54. As shown in FIG. 9B, the dovetail projection 46 has mating surfaces 84a, 84b that are complimentary to the inclined surfaces 78 of the dovetail recess 48. Pivoting the blade 16 presses the inclined surfaces 78 against the mating surfaces 84 and further fixes the blade 16 to the slider assembly 18.

The retractor blade 16 preferably includes the dovetail recess 48 with the locking surface 52 disposed within the recess 48, as shown in FIG. 10A. The retractor blade 16 also includes radiuses 86a, 86b positioned on either side of the dovetail recess 48 that provide clearance between the blade 16 and the slider assembly end portion 44. Alternatively, the slider assembly end portion 44 may include complimentary surfaces that abut the radiuses 86a, 86b and provide further rigidity to the connection between the blade 16 and the slider assembly 18. The blade 16 also has inclined surfaces 78a, 78b disposed within the recess 48 that are inclined relative toward one another and extend from the locking surface 52 to the radiuses 86a, 86b, as shown in FIG. 10B.

In one embodiment, a locking mechanism subassembly 88 comprises the handle 22 connected to the wedge pin 54, as shown in FIGS. 11A-11C. The handle 22 includes an elongate portion 90 and a bent portion 92 separated by a bend 94. The handle 22 may also include a leg 96 projecting from the elongate portion 90. Preferably, the leg 96 is sized so that an end 98 of the leg 96 will contact the slider assembly end portion 44 if the handle 22 is rotated beyond the locked position. This way, the leg 96 resists over-tightening of the blade 16 to the slider assembly 18. To unlock the handle 22, the bent portion 92 may have a tapered section 100 that provides finger clearance to get underneath the handle 22 and rotate the handle 22 to the unlocked position.

The locking mechanism subassembly 88 may be assembled onto the slider end portion 44 in the manner shown in FIG. 12. The end portion 44 may have a bore 102 with a larger opening 104, the bore 102 being configured to receive an enlarged portion 106 of the wedge pin 54 that is preferably threaded. The opening 104 is sized to receive the wedge pin head portion 70 and has a depth that permits the wedge pin contact surface 72 to be flush with the slider assembly confronting surface 50. To assemble the locking mechanism subassembly 88 to the end portion 44, the wedge pin shaft portion 66 is inserted through the bore 102 and into the handle bore 68. At this point, the wedge pin shaft portion 66 may be rigidly connected to the handle 22 using a press fit engagement, a locking pin, epoxy, or the preferred approach, a spot weld.

Figure 13:
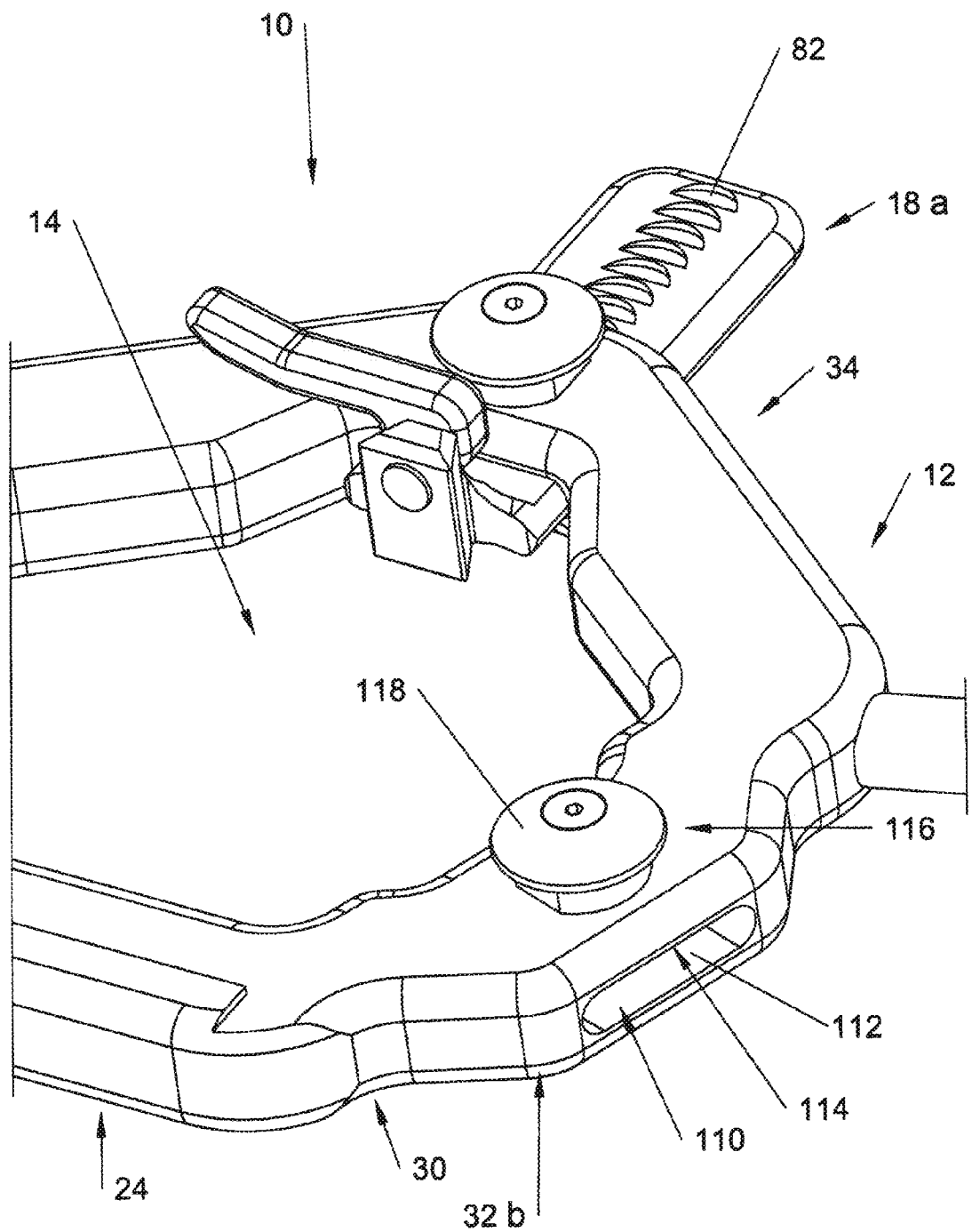
FIG. 13 is a perspective view of the access retractor of FIG. 1 with the retractor blades and a slider assembly removed to show a slide connection configured such that the removed slider assembly retracts in a direction transverse to a retractor body straight portion.

Turning now to more details of the slide connection 32, the access retractor 10 is shown in FIG. 13 with the blades 16a, 16b, 16c and slider assembly 18c removed. Slide connection 32b is positioned in opposed retractor body portion 30 and may include an opening 110 that extends through the body portion 30. A pair of opposed flat surfaces 112, 114 extend along the opening 110 and provide smooth surfaces for the slider assembly 18 to slide along. The slide connection 32 may also include a plunger assembly 116 with a plunger head (not shown) that engages ratchet teeth 82 of the slider assembly 18. Further details of the plunger assembly 116 are disclosed in U.S. Patent Application Publication Number 2009/0069635 to Gephart et al., which published on Mar. 12, 2009, the entirety of which is fully incorporated by reference as if set forth herein.

The plunger assembly 116 permits the slider assembly 18 to slide freely into the retracted position, but resists movement of the slider assembly 18 toward the unretracted position. To return the slider assembly 18 to the unretracted position, the disc handle 300 must be pulled away from the retractor body 12 to release the plunger head from the ratchet teeth 82. This operation permits rapid retraction of an incision and resists tissue forces which tend to collapse the blades to their unretracted position. The slide connection 32 may take a variety of forms, including a channel formed in the retractor body 12 or even a separate structure for receiving the slider assembly 18. Further, the slide connection 32 may utilize a clamping mechanism or other device to keep the slider assembly 18 in the retracted position.

Figure 14:
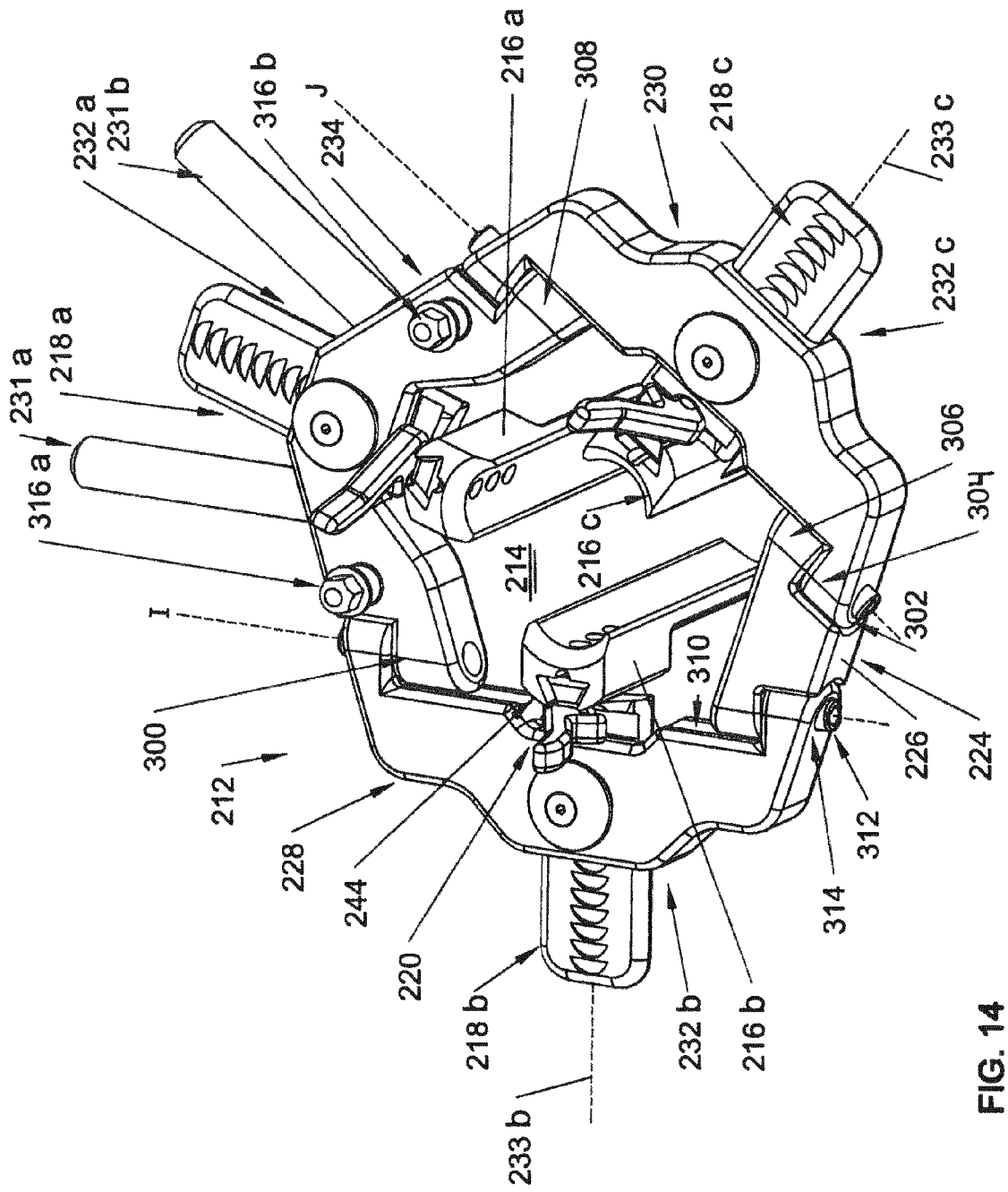
FIG. 14 is a perspective view of another access retractor in accordance with the present invention including pivoting opposed retractor body portions.
Figure 15:
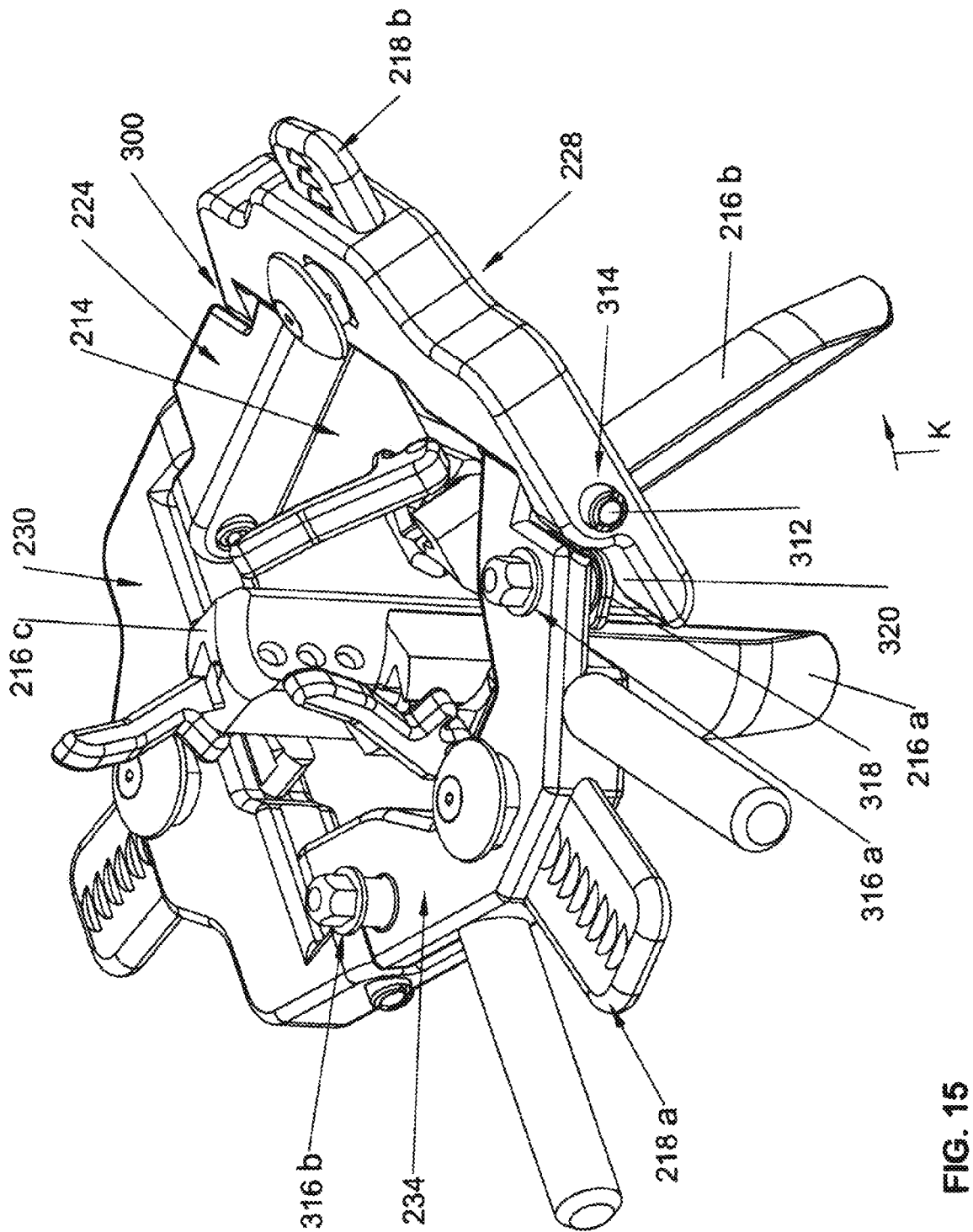
FIG. 15 is a perspective view of the access retractor of FIG. 14 showing one of the opposed retractor body portions pivoted upward which toes out the associated retractor blade.

Another access retractor embodiment 210 is shown in FIGS. 14 and 15. The retractor 210 has a frame or body 212 that includes a straight portion 224 with a flat surface 226 configured to be placed adjacent a bone. A pair of opposed retractor body portions 228, 230 are connected at either end of the straight portion 224 and both extend transversely to the straight portion 224. The retractor body 212 may also have posts 231a, 231b that are configured to be held by a support structure which stabilizes the retractor 210, such as an Iron Intern®. The retractor 210 preferably includes slider assemblies 218a, 218b, and 218c having end portions 244 disposed within the retractor body opening 214 to which retractor blades 216a, 216b, 216c are connected. A pair of slide connections 232b, 232c join the slider assemblies 218a, 218b to the opposed retractor body portions 228, 230. The slide connections 232b, 232c are configured so that the slider members 218b, 218c and attached blades 216b, 216c advance and retract along axes 233b, 233c, which are transverse to the straight portion 224.

In one form, the opposed retractor body portions 228, 230 are pivotal about respective axes I, J relative to the straight portion 224. A bridge retractor body portion 234 is positioned opposite the straight portion 224 and is wider than the straight portion 224 such that the pivot axes I, J are closer adjacent the straight portion 224 than adjacent the bridge portion 234. The retractor body 212 also has features that permit the opposed retractor body portions 228, 230 to pivot. For example, a pivot hinge 300 may be positioned at either end of the opposed body portions 228, 230 and includes a rounded projection 302 of the body portions 228, 230 and a curved recess 304 of the straight or bridge body portions 224, 234. Similarly, the straight and bridge body portions 224, 234 may have rounded projections 306, 308 that are in close relation to a complimentary undercut 310 formed in the opposed body portions 228, 230.

The pivot hinges 300 restrict movement of the retractor body portions 228, 230 to pivotal movement upward from the plane generally defined by the straight portion 224 and the bridge portion 234, as shown in FIG. 15. More specifically, each pivot hinge 300 includes a bolt 312 received within a bore 314 which connects the opposed retractor body portions 228, 230 to either the straight portion 224 or the bridge portion 234. Adjustment screws 316a, 316b may be positioned within bores in the retractor body bridge portion 234 such that driving the adjustment screws 316a, 316b into the retractor body 212 pivots the corresponding body portion 228, 230 upward.

For example, the adjustment screw 316a may have a foot 318 that contacts an adjustment surface 320 of the opposed retractor body portion 228, so that shifting the adjustment surface 320 downward pivots the opposed retractor body portion 228 upward, as shown in FIG. 15. Pivoting the body portion 228 "toes out" the blade 216b in direction K and permits the retractor body 212 to conform to the curvature of the patient's anatomy. Toeing out the blade 216b is advantageous when a surgeon requires additional space to operate deeper within the incision, as moving the blade 216b in direction K increases the width of a working area within an incision. Toeing out a retractor blade 216 is particularly useful when laterally implanting a bone plate onto the anterior surfaces of a patient's vertebrae. Specifically, expanding the blades 216 near the anterior surfaces permits a surgeon to insert an elongate bone plate lengthwise into the operating channel and rotate the bone plate within the incision to align the length of the bone plate with the target vertebrae. This way, the incision may be smaller than the length of the bone plate.

With respect to material selection, it is preferred that the retractor bodies 12, 212 be formed from 6061 aluminum. However, the retractor bodies 12, 212 may also be made from carbon-fiber reinforced polyetheretherketone (PEEK). The blades 16, 216 are made of aluminum and are radiolucent. The slider assemblies 18, 218 are formed from anodized titanium, while the handles 22, 222 are formed from stainless steel. The components of the access retractors 10, 210 can be readily disassembled and are suitable for sterilization, such as in an autoclave.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. An access retractor for enlarging an incision during lateral approach surgery, the retractor comprising:
a retractor body having an opening, the retractor body generally extending in a plane about the opening;
a generally straight portion of the retractor body having a substantially flat surface for being placed adjacent a bone;
a pair of opposed retractor body portions that both extend transversely to the generally straight portion;
a pair of pivot joints that pivotally connect the opposed retractor body portions to opposite ends of the generally straight portion of the retractor body and permit the opposed retractor body portions to pivot transversely to the plane;
a pair of slider members having end portions disposed within the retractor body opening to which tissue engagement members are connected;
a pair of slide connections between the slider members and the opposed retractor body portions with each slide connection disposed along a respective one of the opposed retractor body portions offset a predetermined distance from the pivot joint that connects the one opposed retractor body portion to the generally straight portion of the retractor body and configured so that the slider members and connected tissue engagement members are retracted directions extending transverse to the straight portion to avoid contact with the bone against which the flat surface of the retractor body straight portion is engaged; and
the generally straight portion of the retractor body being free of any slider member slide connections between the opposite ends thereof.

2. The access retractor of claim 1 wherein the retractor body includes a bridge portion opposite the straight portion that is wider than the straight portion and extends between the opposed retractor body portions to orient the opposed retractor body portions at an incline relative to each other with the slider members retracting in directions transverse to one another.

3. The access retractor of claim 2 including another slider member having an end portion disposed within the retractor body opening and a slide connection between the slider member and the retractor body bridge portion with the slider member and a connected tissue engagement member being retractable in a direction transverse to the retraction directions of the slider members connected to the opposed retractor body portions.

4. The access retractor of claim 2 further comprising a second pair of pivot joints that pivotally connect the opposed retractor body portions to the bridge portion of the retractor body.

5. The access retractor of claim 1 wherein at least one of the slider members includes a locking mechanism with a clamping lever pivotal between an unlocked position that allows the tissue engagement member to be slidably adjusted upwardly or downwardly to a selected depth in the incision, and a locked position that fixes the tissue engagement member at a selected depth in the incision.

6. The access retractor of claim 1 wherein the pair of opposed retractor body portions are pivotal relative to the straight portion about corresponding pivot axes and the retractor body has a bridge portion opposite the straight portion that is wider than the straight portion such that the pivot axes are closer adjacent the straight portion than adjacent the bridge portion.

7. An access retractor for enlarging an incision during lateral approach surgery, the retractor comprising:
a retractor body having an opening;
a generally straight portion of the retractor body having opposite ends and a substantially flat surface extending between the opposite ends for being placed against a bone;
a pair of opposed retractor body portions each having opposite ends and which both extend transversely to the generally straight portion;
a pair of pivot joints that pivotally connect ends of the opposed retractor body portions to the opposite ends of the generally straight portion of the retractor body, the pivot joints configured to permit the opposed retractor body portions to pivot to extend in an upward and transverse direction relative to the generally straight portion with the generally straight portion extending generally horizontally;
a bridge portion of the retractor body opposite the generally straight portion that extends between the opposed retractor body portions;
first, second, and third slider members having end portions disposed within the retractor body opening to which tissue engagement members are connected;
a first slide connection along a first one of the opposed retractor body portions between the first slider member and the first opposed retractor body portion intermediate the opposite ends thereof that restricts movement of the first slider member to linear movement along a single, first axis;
a second slide connection along a second one of the opposed retractor body portions between the second slider member and the second opposed retractor body portion intermediate the opposite ends thereof that restricts movement of the second slider member to linear movement along a single, second axis with the second slide connection configured to orient the second axis to extend obliquely relative to the first axis; and
a third slide connection along the bridge portion between the third slider member and the bridge portion that restricts movement of the third slider member to linear movement along a single, third axis with the third slide connection configured to orient the third axis to extend obliquely to the first and second axes and form angles with the first and second axes that are substantially the same,
wherein the first, second, and third slider members are fixed at oblique angles relative to each other and are capable of linear movement when fixed at said angles.

8. The access retractor of claim 7 wherein the third slide connection is configured to orient the third axis to extend perpendicular to the generally straight portion of the retractor body.

9. The access retractor of claim 7 wherein the access retractor only has three slider members and three slide connections.

10. The access retractor of claim 7 wherein the bridge portion of the retractor body is wider than the generally straight portion of the retractor body to orient the opposed retractor body portions at an incline relative to each other.

11. An access retractor for enlarging an incision during lateral approach surgery, the retractor comprising:
a retractor body having an opening, the retractor body generally extending in a plane about the opening;

a bone-engaging portion of the retractor body for being placed adjacent a bone;

a pair of opposed retractor body portions that both extend transversely to the bone-engaging portion;

a pair of pivot joints that pivotally connect the opposed retractor body portions to opposite ends of the bone-engaging portion of the retractor body and permit the opposed retractor body portions to pivot transversely to the plane;

a pair of slider members having end portions disposed within the retractor body opening to which tissue engagement members are connected;

a pair of slide connections between the slider members and the opposed retractor body portions with each slide connection disposed along a respective one of the opposed retractor body portions offset a predetermined distance from the pivot joint that connects the one opposed retractor body portion to the bone-engaging portion of the retractor body and configured so that the slider members and connected tissue engagement members are retracted in directions extending transverse to the bone-engaging portion to avoid contact with the bone against which the bone-engaging portion of the retractor body is engaged; and the bone-engaging portion of the retractor body being free of any slider member slide connections between the opposite ends thereof.

12. The access retractor of claim 11 wherein the retractor body includes a bridge portion opposite the bone-engaging portion that is wider than the bone-engaging portion and extends between the opposed retractor body portions to orient the opposed retractor body portions at an incline relative to each other with the slider members retracting in directions transverse to one another.

13. The access retractor of claim 12 including another slider member having an end portion disposed within the retractor body opening and a slide connection between the slider member and the retractor body bridge portion with the slider member and a connected tissue engagement member being retractable in a direction transverse to the retraction directions of the slider members connected to the opposed retractor body portions.

14. The access retractor of claim 12 further comprising a second pair of pivot joints that pivotally connect the opposed retractor body portions to the bridge portion of the retractor body.

15. The access retractor of claim 11 wherein the pair of opposed retractor body portions are pivotal relative to the bone-engaging portion about corresponding pivot axes and the retractor body has a bridge portion opposite the bone-engaging portion that is wider than the bone-engaging portion such that the pivot axes are closer adjacent the bone-engaging portion than adjacent the bridge portion.

16. The access retractor of claim 11 wherein the bone engaging portion of the retractor body includes a generally straight portion having a substantially flat surface.

17. An access retractor for enlarging an incision during lateral approach surgery, the retractor comprising:

a retractor body having an opening;

a bone-engaging portion of the retractor body having opposite ends;

a pair of opposed retractor body portions each having opposite ends and which both extend transversely to the bone-engaging portion;

a pair of pivot joints that pivotally connect ends of the opposed retractor body portions to the opposite ends of the bone-engaging portion of the retractor body, the pivot joints configured to permit the opposed retractor body portions to pivot to extend in an upward and transverse direction relative to the bone-engaging portion with the bone-engaging portion extending generally horizontally;

a bridge portion of the retractor body opposite the bone-engaging portion that extends between the opposed retractor body portions;

first, second, and third slider members having end portions disposed within the retractor body opening to which tissue engagement members are connected;

a first slide connection along a first one of the opposed retractor body portions between the first slider member and the first opposed retractor body portion intermediate the opposite ends thereof that restricts movement of the first slider member to linear movement along a single, first axis;

a second slide connection along a second one of the opposed retractor body portions between the second slider member and the second opposed retractor body portion intermediate the opposite ends thereof that restricts movement of the second slider member to linear movement along a single, second axis with the second slide connection configured to orient the second axis to extend obliquely relative to the first axis; and a third slide connection along the bridge portion between the third slider member and the bridge portion that restricts movement of the third slider member to linear movement along a single, third axis with the third slide connection configured to orient the third axis to extend obliquely to the first and second axes and form angles with the first and second axes that are substantially the same, wherein the first, second, and third slider members are fixed at oblique angles relative to each other and are capable of linear movement when fixed at said angles.

18. The access retractor of claim 17 wherein the third slide connection is configured to orient the third axis to extend perpendicular to the bone-engaging portion of the retractor body.

19. The access retractor of claim 17 wherein the access retractor only has three slider members and three slide connections.

20. The access retractor of claim 17 wherein the bridge portion of the retractor body is wider than the bone-engaging portion of the retractor body to orient the opposed retractor body portions at an incline relative to each other.

21. The access retractor of claim 17 wherein the bone-engaging portion of the retractor body includes a generally straight portion having a substantially flat surface extending between the opposite ends of the bone-engaging portion.

* * * * *